United States Patent [19]

Gibboney, Jr.

[11] Patent Number: 5,300,266
[45] Date of Patent: Apr. 5, 1994

[54] ELECTRICAL APPARATUS AND METHOD FOR GENERATING ANTIBIOTIC

[75] Inventor: James W. Gibboney, Jr., Conyers, Ga.

[73] Assignee: Scientific Products Corporation, Conyers, Ga.

[21] Appl. No.: 889,167

[22] Filed: May 27, 1992

[51] Int. Cl.$^5$ .............................................. B01J 19/12
[52] U.S. Cl. ............................ 422/186.07; 422/186.08
[58] Field of Search ...................... 422/28, 186, 186.03, 422/186.04, 186.07, 186.08, 186.12, 186.13, 186.15, 186.18, 186.21, 186.26, 186.28; 204/176

[56] References Cited

U.S. PATENT DOCUMENTS

| | | | |
|---|---|---|---|
| 3,005,762 | 10/1961 | Fenn | 422/186 |
| 3,090,745 | 5/1963 | Berghaus | 422/186 |
| 3,332,870 | 7/1967 | Orbach et al. | 422/186 |
| 3,842,286 | 10/1974 | Imris | 250/535 |
| 4,048,668 | 9/1977 | Von Bargen et al. | 361/235 |
| 4,062,748 | 12/1977 | Imris | 204/176 |
| 4,220,545 | 9/1980 | Franzen et al. | 250/530 |
| 4,221,972 | 9/1980 | Oppal et al. | 250/531 |
| 4,417,966 | 11/1983 | Krauss et al. | 204/176 |
| 4,818,355 | 4/1989 | Kanter et al. | 204/170 |
| 4,929,319 | 5/1990 | Dinter et al. | 204/164 |
| 5,002,738 | 3/1991 | Pin et al. | 422/186.13 |
| 5,061,462 | 10/1991 | Suzuki et al. | 422/186.04 |
| 5,098,671 | 3/1992 | Shiota | 422/186.07 |

*Primary Examiner*—Donald P. Walsh
*Assistant Examiner*—Daniel Jenkins
*Attorney, Agent, or Firm*—Michael A. Mann

[57] ABSTRACT

Apparatus and method for generating negatively charged molecules of the form $[MO_x]$-where M is a positive ion, O is Oxygen and x is a number at least equal to 3. The apparatus comprises a specially shaped anode and cathode spaced apart from each other in a non-conducting housing. The anode has a first portion comprising a long shaft with a support to the housing at one end and a grid at the other end, and a second portion attached to the first comprising a plurality of electrodes. The electrodes are connected together at the end attached to the shaft and separated at their other end, the end toward the cathode. The cathode is in the form of a grid attached to a conductor rod carrying a resistor. When a substantially constant voltage is applied across the anode and cathode, through the shaft and conductor rod, respectively, a plasma forms between and around them that in turn forms a magnetic field around the plasma and the shaft. Diatomic oxygen molecules enter the housing and are polarized by the magnetic field and the resulting oxygen ions accelerated toward the plasma. The plasma excites and confines the oxygen ions long enough for them to strike the materials forming the cathode and anode, releasing positive ions of the cathode and anode materials which bind together and form the negatively charged molecule that is expelled from the apparatus. Once outside the apparatus, the molecules attach themselves to surfaces, neutralize electrically and the excess oxygen atoms oxidize molds, mildews, fungus, and bacteria.

14 Claims, 2 Drawing Sheets

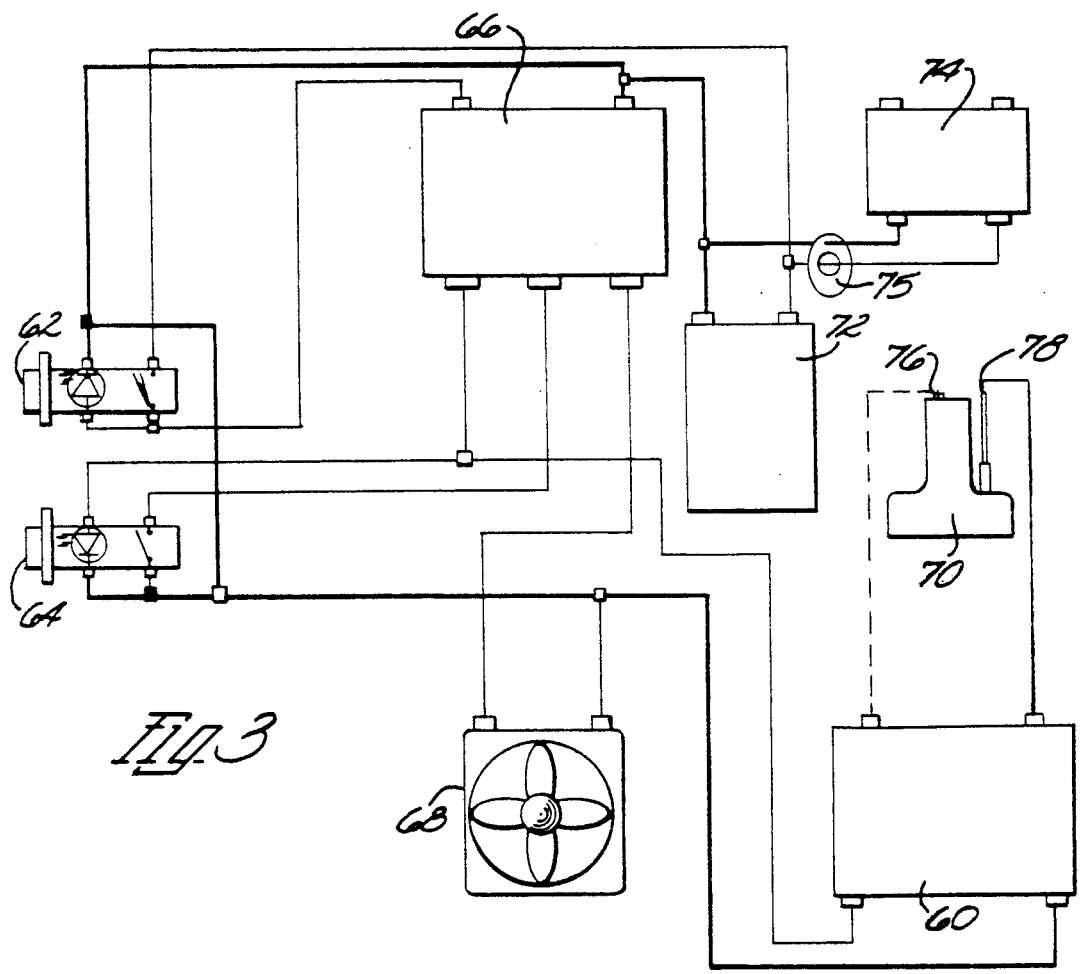

ns, O is oxygen,
ELECTRICAL APPARATUS AND METHOD FOR GENERATING ANTIBIOTIC

BACKGROUND OF THE INVENTION

1. Field of the Invention

The present invention relates to electrical apparatus for generating an antibiotic. In particular, the present invention relates to methods and apparatus for generating, using DC current, negatively charged molecules of the form $[MO_x]^-$, where M is a positive ion, O is oxygen, and x is a number at least 3, which compounds are useful for disinfecting, deodorizing and sanitizing.

2. Discussion of Background

Ozone is recognized as a substance that can be used for oxidizing many substances and also for disinfecting, deodorizing and sanitizing since ozone reacts with water to form hydrogen peroxide, a well known antibiotic. Industrial demand for ozone as an oxidant is strong. However, ozone and other disinfectants, deodorants and sanitizers, such as household cleansers, detergents, sprays, air fresheners, air filters, and the like, have a great many applications for business and private use.

A number of ozone generators exist, most of them operating on alternating current. There are two known to use direct current, that is, a current that does not change polarity, namely, those described in U.S. Pat. No. 4,417,966 issued to Krauss, et al. and in U.S. Pat. No. 4,048,668 issued to Von Bargen et al, but these both use a time-varying current level. The former patent describes a device with a current chopped at a frequency of about 350 Hz; the latter describes a pulsed current having a frequency of ten to sixteen kHz.

Many of these ozone generators require cooling mechanisms to dissipate the quantities of heat produced in the generation of ozone, or systems that operate at an elevated pressure. Notwithstanding the number of these types of generators, there is a continuing need for a generator of an antibiotic that will disinfect, sanitize and deodorize quickly, completely, effectively and do so without the inconvenience of spraying liquids, washing or other fluid treatments that require an undue time for surfaces to dry or for volatile chemicals to dissipate.

SUMMARY OF THE INVENTION

According to its major aspects and broadly stated, the present application is an apparatus for making an antibiotic from diatomic oxygen. The antibiotic is of the form $[MO_x]^-$, where M is a positive ion, O is oxygen, and x is a number having a value equal to or greater than three. The apparatus generates a magnetic field and a plasma field using a substantially constant voltage. The magnetic field causes the diatomic oxygen to separate into oxygen ions and accelerates the ions toward the plasma field. The plasma field temporarily confines the accelerated oxygen ions, long enough for them to bind together. A source of positive ions is in the plasma field, such as, specifically, the cathode and anode that generate the plasma field and define its shape and extent. The cathode and anode are preferably made of soft conductor materials that release positive ions when struck by the oxygen ions. The newly released positive ions and the oxygen ions bind together to form the charged molecules and escape the magnetic field.

The charged molecule produced by the present invention is a very important advantage of the present invention. The particle, being negatively charged and traveling with considerable speed, leaves the apparatus and adheres to and penetrates nearby surfaces. There the charge is quickly neutralized and the oxygen atoms oxidize bacteria, fungus, mold, and mildew on those surfaces. These molecules are unstable and decay to stable forms in a short time. The triatomic form of the molecule (x=3) lasts longest, approximately 20 minutes; the quadratomic form (x=4), decays in about four or five minutes; the quintatomic form (x=5), about one minute. The positive ion helps to bind the addition oxygen ions and makes this negatively charged molecule more stable than ordinary ozone.

Another important feature of the present invention is the combination of magnetic and plasma fields. The magnetic field accelerates the oxygen ions toward the plasma field and encloses that field. The plasma field is established by the application of the voltage, typically on the order of 20 KV, to a specially configured anode and cathode. The plasma field in turn establishes the magnetic field. The two cooperate to pull oxygen molecules apart, reform the resulting ions into the charged molecules, and expel them from the apparatus.

Another important feature of the present invention is the configuration of the anode. The anode comprises a plurality of electrodes, wider at one end than the other and joined together to be in common electrically at the wide end but narrower and separated at the opposing end. The narrow, separated ends of the electrodes are closer to the cathode than the wider, joined ends. This configuration of anode helps to create and shape the plasma field.

Still another feature of the present invention is the cathode, which is in the form of a screen or grid, that is, having a multiplicity of "throughholes" formed in the cathode through which the charged molecules can exit from the apparatus. Because the magnetic field accelerates the charged molecules, they flow toward the cathode. The momentum of these molecules escaping from the plasma field enables them to exit the apparatus as they pass through the holes in the screen or grid.

Still another important feature of the present invention is its adjustability. The gap between anode and cathode can be increased or decreased. Also, a resistor, preferably an adjustable resistor, is carried by the cathode so that the intensity of the plasma field can be changed or adjusted.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 3 is a schematic showing an apparatus according to a preferred embodiment of the present invention in a complete system.

DETAILED DESCRIPTION OF A PREFERRED EMBODIMENT

The present invention is an apparatus and method for producing an antibiotic. The antibiotic is a charged molecule that oxidizes, and thereby destroys, bacteria, mold, fungus, mildew, and odors. The molecule is of the form $[MO_x]^-$, where M is a positive ion, O is oxygen, and x is a number having a value at least equal to three. In particular, x will equal three, four, or five.

The charged molecule is emitted from the apparatus at a speed and, because of its overall negative charge, adheres to surfaces. Because of its speed, it can penetrate short distances into surfaces. Once attached to a surface, be it a wall, a carpet fiber or a dust particle, the charge on the particle is quickly neutralized and the excess oxygens oxidize aggressively all around it. Water or water vapor is converted to hydrogen peroxide, an effective antiseptic itself.

Figure 1:
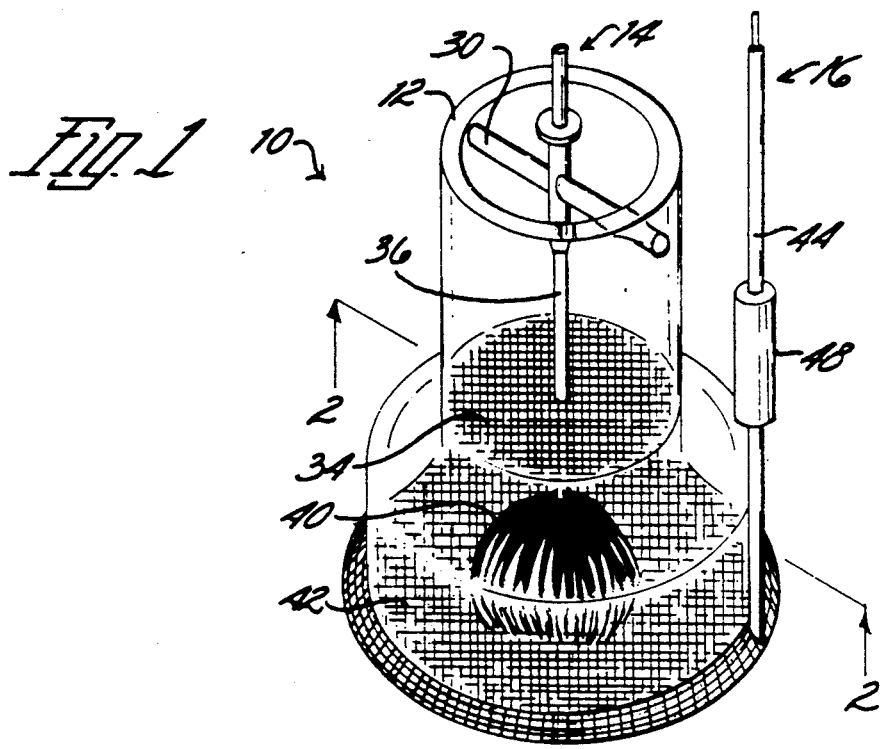
FIG. 1 is a perspective view of an apparatus according to a preferred embodiment of the present invention.
Figure 2:
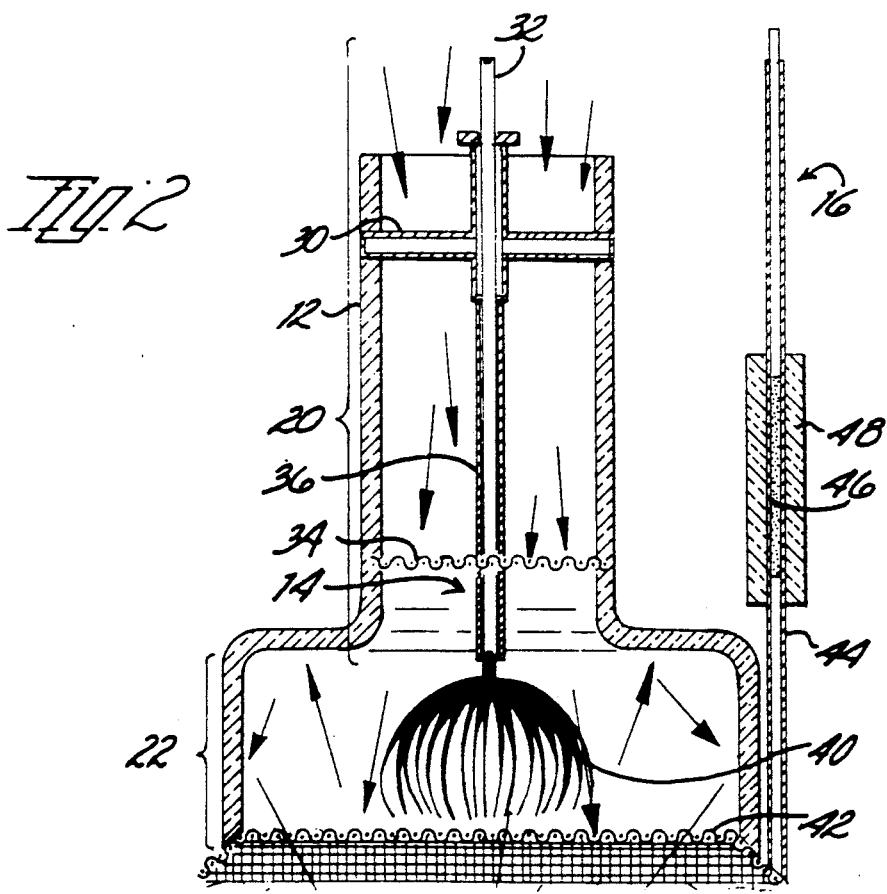
FIG. 2 is a side cross section of the apparatus as shown in FIG. 1 taken along line 2—2.

Referring now to FIGS. 1 and 2, there is illustrated an apparatus according to a preferred embodiment of the present invention. The apparatus, generally indicated by the reference character 10, comprises a housing 12 made of a non-conducting, preferably insulating material, such as glass. Inside is an anode 14. On the end is a cathode 16. Anode 14 has two major portions: a first portion 20 for generating a long electric field; and a second portion 22 for generating a plasma field. The electric field and plasma field generate a magnetic field that pull diatomic oxygen molecules apart, and accelerate them forward toward the plasma and ultimately out of apparatus 10.

First portion 20 comprises a stator bar 30, an anode adjustment shaft 32, a grid 34, and an anode generator shaft 36, all at the same electrical potential. Stator bar 30 provides support for anode 14. Shaft 36 is relatively long so as to produce an elongated electric field in order to create and maintain a high level of ionization of the molecules passing though housing 12. Shaft 36 also acts as a stator to the anode adjustment shaft 32. When a substantially constant voltage is applied across anode 14 and cathode 16, the electrical field thus established along anode generator shaft 36 from stator bar 30 to grid 34 generates a magnetic field oriented so that diatomic oxygen molecules entering housing 12 at 18 will be ionized and accelerated parallel to shaft 36. A voltage of approximately 20 KV is sufficient to generate the magnetic and plasma fields. Housing 12 maintains the oxygen ions, and other ions, at a high state of excitation as they continue through apparatus 10.

Second portion 22 of anode 14 cooperates with cathode 16 in establishing the plasma field. Second portion 22 comprises a plurality of electrodes 40 that flare outwardly from a common attachment to anode adjustment shaft 32. Electrodes 40 are wider at one end, the end where they are in electrical and physical attachment with each other and adjustment shaft 32, and taper toward the opposing end, where they are narrower and separated. Alternatively, electrodes 40 can be interwoven, or in some other configuration, so long as they are separated from each other at the end nearer to cathode 16. The magnetic field encloses the plasma field and assists in the escape of the charged molecules from the confining plasma field.

Cathode 16 is in the form of a grid 42 and a cathode conductor 44 with a cathode resistor 46 and resistor housing 48. Grid 42 can also be in the form of a mesh or perforated plate, so long as it has a plurality of throughholes through which charged molecules, indicated by arrows in FIG. 2, can pass.

Anode adjustment shaft 32 threadedly engages anode generator shaft 36 and has a slot 50 at the end so that, by turning shaft 32, it can be advanced or withdrawn to adjust the size of the gap between anode and cathode 16. An adjustable anode shaft 32 having approximately 32 turns per inch allows sufficient fineness of control for selecting a suitable gap spacing.

Cathode 16 has resistor 46 located within resistor housing 48 of cathode conductor 44 to load cathode 16 and thereby set the intensity of the plasma. If the voltage is 20 KV, the current through apparatus 10 is preferably approximately 250 $\mu$amps, which produces negligible heat. A fan may optionally be used to drive air from the anode side to increase throughput, but is not required since the magnetic field supplies sufficient pressure through the acceleration of the oxygen ions. Thus, no cooling or other special treatment of the incoming air is required in order to produce the charged molecules.

The anode and cathode are preferably two different conductors and also preferably soft, electron-rich materials so that their positive ions can be released by the incident oxygen ions. Soft metals, carbon, fiberglass, or other conductors and semi-conductors are examples of electrode materials that will be satisfactory. In particular, the anode could be made of bronze and the cathode of aluminum. However, there needs to be a source of positive ions and there needs to be an anode and a cathode. The present apparatus combines these requirements in an anode and cathode made of conductor materials that will release positive ions when struck by oxygen ions accelerated by the magnetic field.

In use, as illustrated in FIG. 3, the generator electronic module 60 is activated by two switches 62, 64. Switch 64 is a main power switch which activates a control electronics module 66 and a fan 68. Switch 64 is preferably a "momentary" switch, that is, it does not remain in the "on" position. Switch 64 signals control electronics module 66 to activate generator electronics module 60 which in turn activates apparatus 70. After a preselected period of time, apparatus is turned off by generator electronics module 60. Fan 68 may remain on for a while longer to purge the system.

Power is supplied either by a battery 72 or a standard source of 120 VAC 74 rectified by a rectifier 75.

Generator electronics module generates a high voltage, preferably about 20 KV, which is applied across anode 76 and cathode 78 of apparatus 70. Anode 76 and cathode 78 generate a high-density electrical field which in turn generates a high density plasma field around and between anode 76 and cathode 78, which magnetic field in its turn generates a high density magnetic field inside apparatus 70. The magnetic field encloses and encapsulates the plasma field and runs the length of the electrical field. The magnetic field polarizes the incoming diatomic oxygen, which are then separated into oxygen ions by magnetic repulsion, electrical excitation and high velocity molecular collisions. The magnetic field accelerates the oxygen ions toward anode 76 and cathode 78. The oxygen ions strike anode 76 and cathode 78, causing positive ions from the anode and cathode conductor material to be released. In the plasma, these ions reach a high level of excitation and number of excitation collision coincidences. The oxygen ions bond with each other and with ions released from anode 76 and cathode 78 to form the negatively-charged, triatomic, quadratomic, and quintatomic molecules. These molecules, having more momentum than the individual oxygen ions, escape the plasma and charge toward cathode 78. The charged molecule will pass through holes in cathode 78 and exit apparatus 70.

It will be apparent to those skilled in the art that many changes and substitutions can be made to the preferred embodiment herein described without departing from the spirit and scope of the present invention as defined by the appended claims.

What is claimed is:

1. Apparatus for use with a source of direct electrical current and a source of oxygen, said apparatus comprising:

a housing made of a non-electrically conducting material, said housing having a first opening for oxygen from said source of oxygen to enter said housing and a second, opposing opening;

a cathode positioned in said housing near said first opening, said cathode having a plurality of throughholes through which said oxygen can pass; and an anode positioned in said housing and spaced apart from said cathode so as to define a gap therebetween, said anode having a first portion near said second opening and an adjacent second portion, said first portion formed to accelerate ions electromagnetically from said housing through said second opening when said source of direct electrical current is applied across said anode and cathode, said second portion being in the form of a plurality of electrodes flaring outwardly and toward said cathode so as to form a plasma between said second portion and said cathode when said electrical current is applied to said cathode and said anode, said plasma ionizing said oxygen entering said housing through said first opening and producing a charged molecule that is accelerated by said first portion of said anode through and from said housing.

2. The apparatus as recited in claim 1, wherein said anode and said cathode are made of different conductors.

3. The apparatus as recited in claim 1, further comprising means for changing said gap.

4. The apparatus as recited in claim 1, wherein said cathode is in the form of a grid.

5. The apparatus as recited in claim 1, wherein said plurality of electrodes of said anode are tapered.

6. The apparatus as recited in claim 1, wherein said electrodes of said anode are interwoven.

7. The apparatus as recited in claim 1, wherein said apparatus has means for adjusting the intensity of said plasma.

8. Apparatus for use with a source of direct electrical current and a source of oxygen, said apparatus comprising:

a housing made of a non-electrically conducting material, said housing having a first opening for oxygen from said source of oxygen to enter and a second, opposing opening;

a cathode positioned in said housing near said first opening, said cathode having a plurality of throughholes for said oxygen to flow therethrough; and an anode positioned in said housing and spaced apart from said cathode so as to define a gap therebetween, said anode having a conducting rod at one end near said second opening, and a plurality of electrodes flaring outwardly and toward said cathode at said opposing second end, so that, when said electrical current is applied to said anode and said cathode, said plurality of electrodes form a plasma with said cathode that ionizes said oxygen entering said first opening, and said conducting rod accelerates electromagnetically ions escaping said plasma toward said second end and from said housing.

9. The apparatus as recited in claim 8, wherein said plurality of electrodes are woven together.

10. The apparatus as recited in claim 8, wherein said cathode is in the form of a grid.

11. The apparatus as recited in claim 8, wherein said anode and said cathode are made of different conductors.

12. The apparatus as recited in claim 8, further comprising means for changing said gap.

13. The apparatus as recited in claim 8, further comprising a resistor in series with said cathode for adjusting the intensity of said plasma.

14. The apparatus as recited in claim, further comprising a source of positive ions positioned between said anode and said cathode.

* * * * *